United States Patent
Olivares et al.

(10) Patent No.: US 9,624,533 B2
(45) Date of Patent: Apr. 18, 2017

(54) MULTIPLEX NUCLEIC ACID DETECTION METHODS

(71) Applicant: INVITAE CORPORATION, San Francisco, CA (US)

(72) Inventors: Eric Olivares, San Francisco, CA (US); Jon Sorenson, San Francisco, CA (US); Tom Landers, San Francisco, CA (US)

(73) Assignee: INVITAE CORPORATION, San Francisco, CA (US)

( * ) Notice: Subject to any disclaimer, the term of this patent is extended or adjusted under 35 U.S.C. 154(b) by 0 days.

(21) Appl. No.: 14/099,821

(22) Filed: Dec. 6, 2013

(65) Prior Publication Data
US 2014/0235470 A1   Aug. 21, 2014

Related U.S. Application Data

(60) Provisional application No. 61/734,838, filed on Dec. 7, 2012.

(51) Int. Cl.
*C12Q 1/68* (2006.01)
*C12P 19/34* (2006.01)

(52) U.S. Cl.
CPC .......... *C12Q 1/6827* (2013.01); *C12Q 1/686* (2013.01); *C12Q 1/6874* (2013.01); *C12Q 2537/16* (2013.01)

(58) Field of Classification Search
CPC ...... C12Q 1/68; C12Q 1/6813; C12Q 1/6827; C12Q 1/6832; C12Q 1/6844;
(Continued)

(56) References Cited

U.S. PATENT DOCUMENTS 4,683,195 A   7/1987   Mullis et al.
4,683,202 A   7/1987   Mullis
(Continued)

FOREIGN PATENT DOCUMENTS

WO   WO 2005/068656      7/2005
WO   WO 2011/071923 A2   6/2011
(Continued)

OTHER PUBLICATIONS

Stiller et al., "Direct multiplex sequencing (DMPS)—a novel method for targeted high-throughput sequencing of ancient and highly degraded DNA," Genome Research, 2009, vol. 19, pp. 1843-1848.*

(Continued)

*Primary Examiner* — Young J Kim
(74) *Attorney, Agent, or Firm* — Pillsbury Winthrop Shaw Pittman, LLP

(57) ABSTRACT

Methods for multiplex ligation-dependent probe amplification include (a) providing a sample tissue to query different target nucleic acids, (b) providing different probe sets for each of the target nucleic acids, each probe set including a first locus specific probe having a first adapter sequence and a first target specific portion and a second locus specific probe having a second adapter sequence, and a second target specific portion adjacent to the first target specific portion, (c) hybridizing the probe sets to the target sequences to form hybridization complexes, (d) ligating the hybridization complexes to form ligated probes, (e) amplifying the ligated probes to form amplicons, the amplifying step being carried out with a first universal primer including a region complementary to the first adapter sequence and a second universal primer including a region complementary to the second adapter sequence, and (f) detecting the amplicons in a detection system by sequencing each of the amplicons.

15 Claims, 12 Drawing Sheets

(58) Field of Classification Search
CPC ............. C12Q 1/6862; C12Q 1/6869; C12Q 2525/501; C12Q 2525/155; C12Q 2531/10; C12Q 2533/107; C12Q 2537/143; C12Q 2561/125
See application file for complete search history.

(56) References Cited

U.S. PATENT DOCUMENTS

| | | | |
|---|---|---|---|
| 5,508,179 | A | 4/1996 | Wallace et al. |
| 6,027,889 | A * | 2/2000 | Barany et al. ............ 435/6.12 |
| 6,544,732 | B1 | 4/2003 | Chee et al. |
| 7,883,849 | B1 | 2/2011 | Dahl et al. |
| 2009/0215633 | A1 | 8/2009 | Van Eijk et al. |
| 2010/0267585 | A1 * | 10/2010 | Terbrueggen ........ C12Q 1/6855 506/16 |
| 2011/0124518 | A1 * | 5/2011 | Cantor ................ C12Q 1/6816 506/9 |

FOREIGN PATENT DOCUMENTS

| | | |
|---|---|---|
| WO | WO 2011/091106 A2 | 7/2011 |
| WO | 2012018397 A2 | 2/2012 |
| WO | WO 2012/158967 A1 | 11/2012 |

OTHER PUBLICATIONS

Extended European Search Report issued Jun. 13, 2016 in corresponding European Patent Application No. 13860702.3 (8 pages).
Yiping Shen et al., "Designing a simple multiplex ligation-dependent probe amplification (MLPA) assay for rapid detection of copy number variants in the genome", Journal of Genetics and Genomics, May 2009, vol. 36, No. 4, pp. 257-265.
Janneke Rotman et al., "Rapid screening of innate immune gene expression in zebrafish using reverse transcription-multiplex ligation-dependent probe amplification", BMC Research Notes 2011, Jun. 15, 2011 vol. 4, No. 1, 10 pages.
Ana M. Cosialls et al., "Epigenetic profile in chronic lymphocytic leukemia using methylation-specific multiplex ligation-dependent probe amplification", Epigenomics, Future Medicine Ltd, Oct. 2012 ,vol. 4, No. 5, pp. 491-501.
Nicola Dikow et al., "Quantification of the methylation status of the PWS/AS imprinted region: Comparison of two approaches based on bisulfite sequencing and methylation-sensitive MLPA", Molecular and Cellular Probes, Mar. 16, 2007, vol. 21, No. 3, pp. 208-215.
Eijk van Os et al. Multiplex Ligation-Dependent Probe Amplification (MLPA) for the Detection of Copy Number Variation in Genomic Sequences; Methods Mol Biol; (2011); vol. 688; pp. 97-126.
Hoffman et al.; DNA bar coding and pyrosequencing to identify rare HIV drug resistance mutations; Nucleic Acids Res; Jun. 18, 2007; vol. 35; No. 13.
Metzker. Sequencing technologies—the next generation; Nat Rev Gener; Jan. 2010; vol. 11; No. 1; pp. 31-46.
International Search Report and Written Opinion issued Apr. 23, 2014 in corresponding PCT Application No. PCT/US2013/073745.
International Preliminary Report on Patentability dated Nov. 7, 2014 in corresponding PCT Application No. PCT/US2013/073745.
Barany, Francis, "The ligase chain reaction in a PCR world.", PCR Methods and Applications, Nov. 1991, vol. 1, pp. 5-16, downloaded from genome.cshlp.org on Dec. 2, 2016—Published by Cold Spring Harbor Laboratory Press.
Marsh, Edward, et al., "Pyrococcus Furiosus DNA Ligase and the Ligase Chain Reaction," Strategies in Molecular Biology, 1992, vol. 5, pp. 73-76.
Albertson, Donna G. et al., 6th Edition of the Molecular Probes Handbook by Richard P. Haugland, "Chromosome aberrations in solid tumors", Nature Genetics, Aug. 2003, vol. 34, pp. 369-76.
Lengauer, Christoph et al., "Genetic instabilities in human cancers", Nature, Dec. 17, 1998, vol. 396; pp. 643-9.
Nygren, Anders O.H. et al., "Methylation-Specific MLPA (MS-MLPA): simultaneous detection of CpG methylation and copy number changes of up to 40 sequences", Nucleic Acids Research, Aug. 16, 2005, vol. 33:e128.
Illumina. Genome Analyzer IIx User Guide (SCS v2.10) [online] Jul. 2012 [retrieved Mar. 18, 2014]. Available on the internet: <URL: http://www.google.co.th/url?sa=t&rct=j&q=&esrc=s& source=web&cd=1&ved=OCDcQFjAA&url=http%3A%2F%2F supportres.illumina.com %2Fdocuments%2Fmyillumina% 2Fd2aa31 fa-51 aD-48c9-874 7 -edfb 7 48701ff%2Fgaiix__ userguide_scs2-10_15030966_cpdf&ei=ssknU52glc6kigfw 4D4DQ&usg=AFQjCNGdspHbi3WzPPeg5z4Q_zWD7EgAOA& sig2=4y51UDrpfuSisdGTVPOvsg&bvm=bv.62922401,d.aGc>.

* cited by examiner

- Number of reads mapping to each probe were normalized to control
- Female carrier (XX* = het) for exons 49-52del shows ~0.5 signal
- Male carrier (X*Y = null) for exons 49-52del shows 0 signal

MULTIPLEX NUCLEIC ACID DETECTION METHODS

RELATED APPLICATIONS

This application claims priority to U.S. Provisional Application No. 61/734,838, filed Dec. 7, 2012, is expressly incorporated herein by reference its entirety.

SEQUENCE LISTING

The instant application contains a Sequence Listing which has been submitted in ASCII format via EFS-Web and is hereby incorporated by reference in its entirety. Said ASCII copy, created on May 5, 2014, is named Invitae0428713_ST25.txt and is 3,434 bytes in size.

BACKGROUND

Embodiments disclosed herein relate to nucleic acids, and more particularly to methods for multiplex detection of target nucleic acid sequences.

Multiplex Ligation-dependent Probe Amplification (MLPA) is a multiplex PCR technique that permits the evaluation of, inter alia, the copy number of several target nucleic acids in a single experiment. In MLPA, each target nucleic acid queried is detected by amplification of a ligated probe. The ligated probe is generated by hybridization and ligation of a probe set comprising a pair of half-probes which are designed to reside adjacent to each other along the target nucleic acid sequence of interest. Only when the half-probes hybridize to the target nucleic acid will ligation and subsequent amplification occur.

FIG. 1 shows a flow diagram for a typical MLPA assay. The assay begins by denaturation of the DNA sample and hybridization of the probe sets to their target nucleic acid sequences. After hybridization, the adjacent half-probes are ligated and the resultant ligated probe sets are subjected to PCR amplification. The amplified ligated probe sets are then analyzed by capillary electrophoresis (CE). The peak height of the CE readout serves as the readout for the genomic target copy number.

As indicated in FIG. 1, each probe set is composed of a 5' and 3' half-probe having a target specific sequence and a universal primer sequence allowing the simultaneous multiplex PCR amplification of all ligated probe sets. Additionally, one (as shown in FIG. 1) or both half-probes further include a stuffer sequence which facilitates differentiation in detection of the amplified probes by CE. The use of these stuffer sequences to enable CE detection based on nucleic acid length has imposed limits on the number of target nucleic acids that may be queried in a single run. Currently, that limit is about 40 target nucleic acids. Because of the low cost, potential for high throughput, and ability to detect small rearrangements associated with MLPA, it would be beneficial to expand the number of target nucleic acid sequences that can be queried in a single run. The present disclosure provides methods for such an expansion in query number and provides related advantages as well.

SUMMARY

According to embodiments illustrated herein, there are provided methods for increasing the number of target nucleic acids that can be queried in the Multiplex Ligation-dependent Probe Amplification (MLPA) assay.

In some aspects, embodiments disclosed herein provide methods for multiplex ligation-dependent probe amplification comprising (a) providing a sample tissue to query a plurality of different target nucleic acids, (b) providing a plurality of different probe sets for each of the plurality of different target nucleic acids, wherein each probe set comprises a first locus specific probe comprising a first adapter sequence and a first target specific portion and a second locus specific probe comprising a second adapter sequence, and a second target specific portion adjacent to the first target specific portion, (c) hybridizing the plurality of different probe sets to the plurality of different target sequences to form a plurality of hybridization complexes, (d) ligating the plurality of hybridization complexes to form a plurality of ligated probes, (e) amplifying the plurality of ligated probes to form a plurality of amplicons, wherein the amplifying step is carried out with a first universal primer comprising a region complementary to the first adapter sequence and a second universal primer comprising a region complementary to the second adapter sequence, and (h) detecting the plurality of amplicons in a detection system, independently of the length, by sequencing each of the plurality of amplicons.

In other aspects, embodiments disclosed herein provide methods comprising providing a detection system comprising a fluidics handling system configured to perform cycles of sequencing by synthesis on an array comprising a plurality of amplicons, the detection system configured to direct radiation from a source to the array and to direct fluorescence emission from the array to a camera, and a system control interface configured to automatically modify the detection system to increase the exposure level of the radiation directed to the array and detect fluorescence emission from the array to the camera at the increased exposure, providing the plurality of amplicons through multiplex ligation-dependent probe amplification, and determining the sequences of the plurality of amplicons.

BRIEF DESCRIPTION OF THE DRAWINGS

For a better understanding of the present embodiments, reference may be made to the accompanying figures.

DETAILED DESCRIPTION

Figure 1:
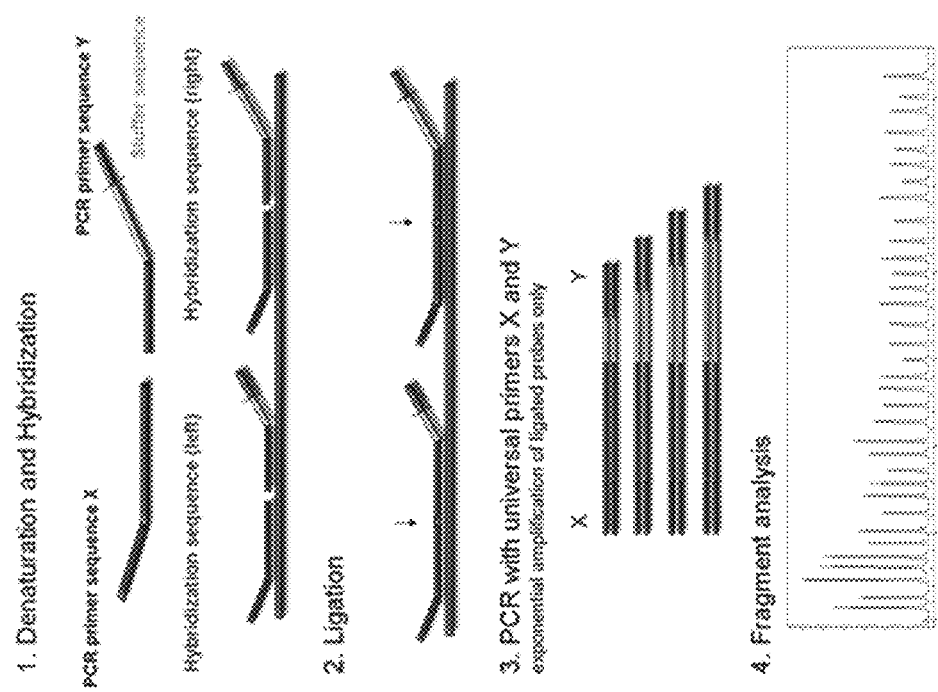
FIG. 1 shows a flow diagram for Multiplex Ligation-dependent Probe Amplification (MLPA) employing capillary electrophoresis detection systems.

In the following description, it is understood that other embodiments may be utilized and structural and operational changes may be made without departure from the scope of the present embodiments disclosed herein.

In accordance with embodiments disclosed herein, there are provided methods that may allow the number of target nucleic acids that can be queried in the Multiplex Ligation-dependent Probe Amplification (MLPA) assay to be substantially increased from the current limitation of about 40 target nucleic acid sequences per run. For example, the use of sequencing-by-synthesis (SBS) systems for the detection of amplified products can remove the query number limitations set by CE-based detection systems. In practical terms, the number of target sequences queried in methods disclosed herein need only be limited by the availability of appropriate probe sets.

Moreover, employing SBS detection systems may simplify probe set design by eliminating the need for stuffer sequences as the means for differentiating amplified probe products and thus, may reduce costs associated with developing probe sets. SBS detection systems may utilize optional indexing of the probe sets in a manner independent of the length of the amplified probe. Advantageously, employing SBS detection systems with indexing may facilitate, for example, simultaneous querying of multiple patient/tissue samples. Finally, SBS detection may provide enhanced detection sensitivity allowing a reduction in sample size relative to CE-based techniques.

In some embodiments, there are provided methods for multiplex ligation-dependent probe amplification comprising (a) providing a sample tissue to query a plurality of different target nucleic acids, (b) providing a plurality of different probe sets for each of the plurality of different target nucleic acids, wherein each probe set comprises a first locus specific probe comprising a first adapter sequence and a first target specific portion, and a second locus specific probe comprising a second adapter sequence, and a second target specific portion adjacent to the first target specific portion, (c) hybridizing the plurality of different probe sets to the plurality of different target sequences to form a plurality of hybridization complexes, (d) ligating the plurality of hybridization complexes to form a plurality of ligated probes, (e) amplifying the plurality of ligated probes to form a plurality of amplicons, wherein the amplifying step is carried out with a first universal primer comprising a region complementary to the first adapter sequence and a second universal primer comprising a region complementary to the second adapter sequence, and (f) detecting the plurality of amplicons in a detection system, independently of the length, by sequencing each of the plurality of amplicons.

Embodiments disclosed herein provide a number of different nucleic acids as primers and probes/probe sets. As used herein, "nucleic acid" or grammatical equivalents means at least two nucleotides covalently linked together. A nucleic acid will generally contain phosphodiester bonds, although in some cases, particularly for use with probes, nucleic acid analogs can be included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048)), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31:1008 (1992); Nielsen, Nature, 365:566 (1993): Carisson et al., Nature 380:207 (1996), all of which are incorporated by reference). Other analog nucleic acids include those with positively charged backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medidicinal Chem. Lett. 4:395 (1994); Jeffs et al., J. Biomolecular NMR 34:17 (1994); Tetrahedron Lett. 37:743 (19986)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169-176). Several nucleic acid analogs are described in Rawls, C & E News Jun. 2, 1997 page 35. The nucleic acids can also be "locked nucleic acids". All of these references are hereby expressly incorporated by reference in their entirety. Modifications of the ribose-phosphate backbone may be done to facilitate the addition of labels, or to increase the stability and half-life of such molecules in physiological environments, for example. As will be appreciated by those skilled in the art, all of these nucleic acid analogs may find use as probes in methods disclosed herein. In addition, mixtures of naturally occurring nucleic acids and analogs can be prepared. Alternatively, mixtures of different nucleic acid analogs, and mixtures of naturally occurring nucleic acids and analogs may be employed.

The size of primers and probe nucleic acids employed in methods disclosed herein may vary, as will be appreciated by those skilled in the art, with each universal primer and each portion of a half-probe and the total length of the half-probe in general varying from about 5 to about 500 nucleotides in length. Each portion of a half-probe in a probe set may be in a range of from about 10 to about 100 nucleotides, from about 15 to about 50 nucleotides, or from about 10 to about 35 nucleotides in length, including all sub-ranges in between. For example, the adapter sequences of the half-probes may be in a range from 15-25 nucleotides in length, with 20 being typical. The target specific portion of each half-probe may be in a range of from about 15 to about 50 nucleotides in length, or from about 30 to about 40 nucleotides in length, including all sub-ranges in between. Thus, the total length of the target sequence in a ligated product (ligation of the two half-probes) may be in a range of from about 30 to about 100 nucleotides in length, or from about 60 to about 80 nucleotides in length, including all sub-ranges in between.

Methods disclosed herein provide a plurality of target probe sets. "Probe sets" encompass the plurality of locus specific half-probe pairs that are used in MLPA assays. In this context, plurality means at least two or at least 10 or at least 50, or at least 100, and so on, depending on the assay, sample and purpose of the test.

By "universal priming site" herein is meant a sequence of the that will bind a PCR primer for amplification. Each half-probe comprises an adapter sequence that provides either an upstream universal priming site (UUP) or a downstream universal priming site (DUP). "Upstream" and "downstream" are not meant to convey a particular 5'-3' orientation, and will depend on the orientation of the system. In addition, the adapter sequences are generally located at the 5' and 3' termini of the half-probe or the ligated products, as only sequences flanked by such priming sequences will be amplified.

In addition, universal priming sequences are generally chosen to be as unique as possible given the particular assays and host genomes to ensure specificity of the assay. In general, universal priming sequences may range in size from about 5 to about 35 nucleotides, with about 20 being typical.

As will be appreciated by those skilled in the art, the orientation of the two priming sites in the ligated probe sets are different. That is, one PCR primer will directly hybridize to the first adapter sequence (first universal priming site), while the other PCR primer will hybridize to the complement of the second adapter sequence (second universal priming site). Stated differently, the first priming site is in sense orientation, and the second priming site is in antisense orientation.

In addition to the adapter sequences used as primer sites, the half-probes comprise at least a first locus-specific sequence, that is substantially complementary to the a portion of the target nucleic acid. As outlined below, ligation probes each comprise a separate portion of an locus-specific sequence. As will be appreciated by those skilled in the art, the locus-specific sequence may take on a wide variety of formats, depending on the use of probe. Although reference is made to "half-probes," this is not intended to mean that the two half-probes spanning a query target nucleic acid need to be complementary to exactly half of the target of the target nucleic acid. For example, the two half probes may be designed to divide a query target nucleic acid into a first locus specific portion comprising a sequence that is complementary to about one third of the target nucleic acid, while the second locus specific portion may be complementary to about two thirds of the target nucleic acid. Moreover, the two half-probes need not necessarily span the entirety of a target nucleic acid sequence. One skilled in the art will appreciate that the exact design choice of appropriate half-probes may be facilitated by, inter alia, computational methods.

In some embodiments, the locus specific sequence may span a splice junction of interest. As outlined herein, the locus specific sequences can be designed to be substantially complementary to sequences at the end of individual alternative exons. By substantially complementary herein is meant that the probes are sufficiently complementary to the target sequences to hybridize under normal reaction conditions, and provide the requisite annealing specificity. Since exons are separated by introns, the detection sequences may reside on different parts of an RNA molecule. Thus an locus specific sequence may comprise two parts: an upstream portion, complementary to the terminus of a first exon, and a downstream portion, complementary to the terminus of a second exon. Only if splicing has occurred and the intervening intron has been excised will the target specific sequence hybridize to the target nucleic sequence under the conditions of the assay.

In embodiments, locus specific probes may comprise allele-specific probes. Thus, the first locus specific probe and second locus specific probe may both be allele specific probes.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5 to about 10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions comprise those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art in addition, cross-linking agents may be added after target binding to cross-link, i.e. covalently attach, the two strands of the hybridization complex.

Thus, the MLPA assays are generally run under stringency conditions allowing formation of the hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, and the like. These parameters may also be used to control non-specific binding, as is generally outlined in U.S. Pat. No. 5,681,697. Thus it may be desirable to perform certain steps at higher stringency conditions to reduce non-specific binding.

After the hybridization complexes are formed the half-probes are ligated and the ligated products may be amplified to form amplicons, which are then detected. This can be done, for example, by PCR amplification. In some embodiments, labels can be incorporated into the amplicons.

Many ligases known in the art may be suitable for use in the methods disclosed herein, e.g. Lehman, Science, 186: 790-797 (1974); Engler et al, DNA Ligases, pages 3-30 in Boyer, editor, The Enzymes, Vol. 15B (Academic Press, New York, 1982); and the like. Some ligases include T4 DNA ligase, T7 DNA ligase, E. coli DNA ligase, Taq ligase, Pfu ligase, and Tth ligase. Protocols for their use are well known, e.g. Sambrook et al (cited above); Barany, PCR Methods an Applications, 1: 5-16 (1991); Marsh et al, Strategies, 5: 73-76 (1992); and the like. Generally, ligases require that a 5' phosphate group be present for ligation to the 3' hydroxyl of an abutting strand. In some embodiments, ligases include thermostable or (thermophilic) ligases, such as pfu ligase, Tth ligase, Taq ligase and AMPLIGASE™ DNA ligase (Epicentre Technologies, Madison, Wis.). AMPLIGASE™ has a low blunt end ligation activity.

In some embodiments, the ligase is one which has the least mismatch ligation. The specificity of ligase can be increased by substituting the more specific $NAD^+$-dependant ligases such as E. coli ligase and (thermostable) Taq ligase for the less specific T4 DNA ligase. The use of NAD analogues in the ligation reaction further increases specificity of the ligation reaction. See, U.S. Pat. No. 5,508,179 to Wallace et al.

In some embodiments, the amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference in their entirety.

In general, PCR may be briefly described as follows. The double stranded ligated probe sets are denatured, generally by raising the temperature, and then cooled in the presence of an excess of a PCR primer, which then hybridizes to the first adapter sequence. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second adapter sequence, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerase include, but are not limited to, the Klenow fragment of DNA polymerase I, SEQUENASE 1.0 and SEQUENASE 2.0 (U.S. Biochemical), T5 DNA polymerase and Phi29 DNA polymerase.

The PCR reaction may be initiated by introducing the ligated probe sets to a solution comprising the universal primers, a polymerase and a set of nucleotides. By "nucleotide" in this context herein is meant a deoxynucleoside-triphosphate (also called deoxynucleotides or dNTPs, e.g. dATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction utilizes two PCR primers (forward and reverse), a polymerase, and a set of dNTPs. As outlined herein, the primers may comprise a label, or one or more of the dNTPs may comprise a label. In some embodiments, at least one of the first universal primer and the second universal primer further comprises an indexing sequence. The use of an indexing sequence such as that described in application WO05068656, the contents of which are incorporated herein by reference in their entirety, allows multiple different samples to be analyzed in the same sequencing run while preserving the identity of each sample.

In some embodiments, the amplicons may be labeled with a detection label. By "detection label" herein is meant a moiety that allows detection. In some embodiments, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Labels include chromophores or phosphors, and fluorescent dyes. Suitable dyes for use in methods disclosed herein include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"; see U.S. Ser. No. 09/315,584, hereby incorporated by reference), pyrene, Malacite green, stilbene, Lucifer Yellow, CASCADE BLUE™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference in its entirety.

Amplicons generated in the PCR amplification step may be analyzed in numerous ways in a manner that is independent of length. In some embodiments, amplicons may be characterized by sequencing-by-synthesis (SBS) methods. Sequencing can be carried out using any suitable "sequencing-by-synthesis" technique, wherein nucleotides are added successively to a free 3' hydroxyl group, typically provided by annealing of a sequencing primer, resulting in synthesis of a polynucleotide chain in the 5' to 3' direction. The nature of the nucleotide added can be determined after each addition.

One suitable sequencing method which can be used in the methods of the invention relies on the use of modified nucleotides that can act as chain terminators. Once the modified nucleotide has been incorporated into the growing polynucleotide chain complementary to the region of the ligated probe being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the nucleic acid sequence of the ligated probe. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. In some such embodiments, this may be a fluorescent label. Each nucleotide type may carry a different fluorescent label. However the detectable label need not be a fluorescent label. Any label can be used which allows the detection of the incorporation of the nucleotide into the nucleic acid sequence.

One method for detecting the fluorescently labeled nucleotides comprises using radiation of a wavelength specific for the labeled nucleotides, or the use of other suitable sources of illumination. The fluorescence from the label on the nucleotide may be detected by a CCD camera or other suitable detection means.

The methods described herein are not limited to use of the sequencing method outlined above, but can be used in conjunction with essentially any sequencing methodology which relies on successive incorporation of nucleotides into a polynucleotide chain. Suitable techniques include, for example, PYROSEQUENCING™, FISSEQ (fluorescent in situ sequencing), MPSS (massively parallel signature sequencing) and sequencing by ligation-based methods. In some embodiments, it is possible to prepare arrays of the ligated probe sets. With the use of arrays it is possible to sequence multiple targets of the same or different sequences in parallel.

Figure 2:
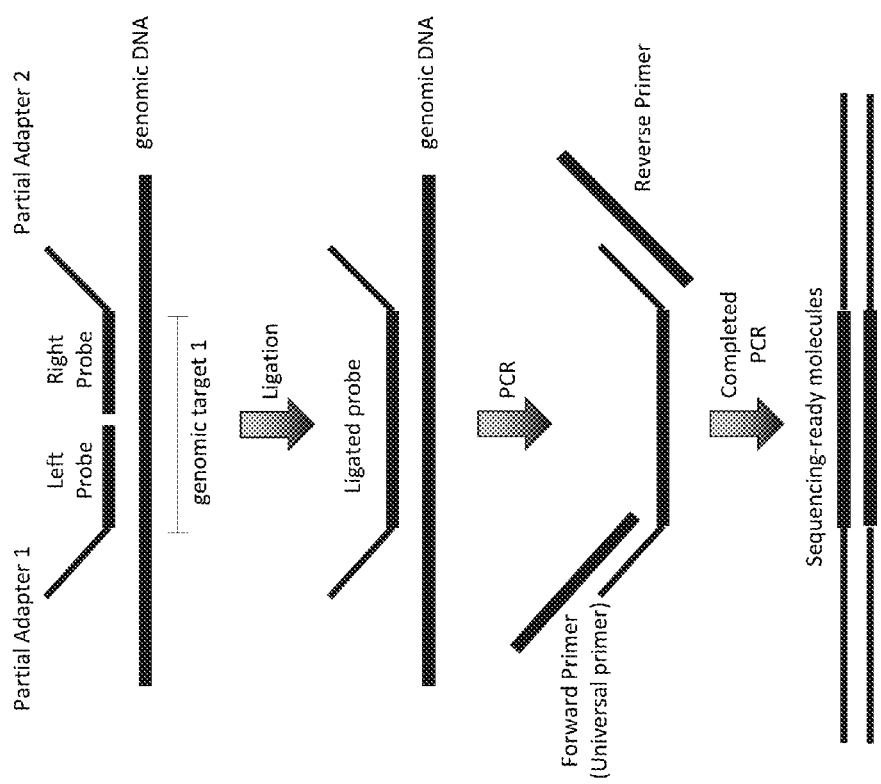
FIG. 2 shows a flow diagram for MLPA-Sequencing-by-Synthesis (SBS), in accordance with embodiments disclosed herein.
Figure 3:
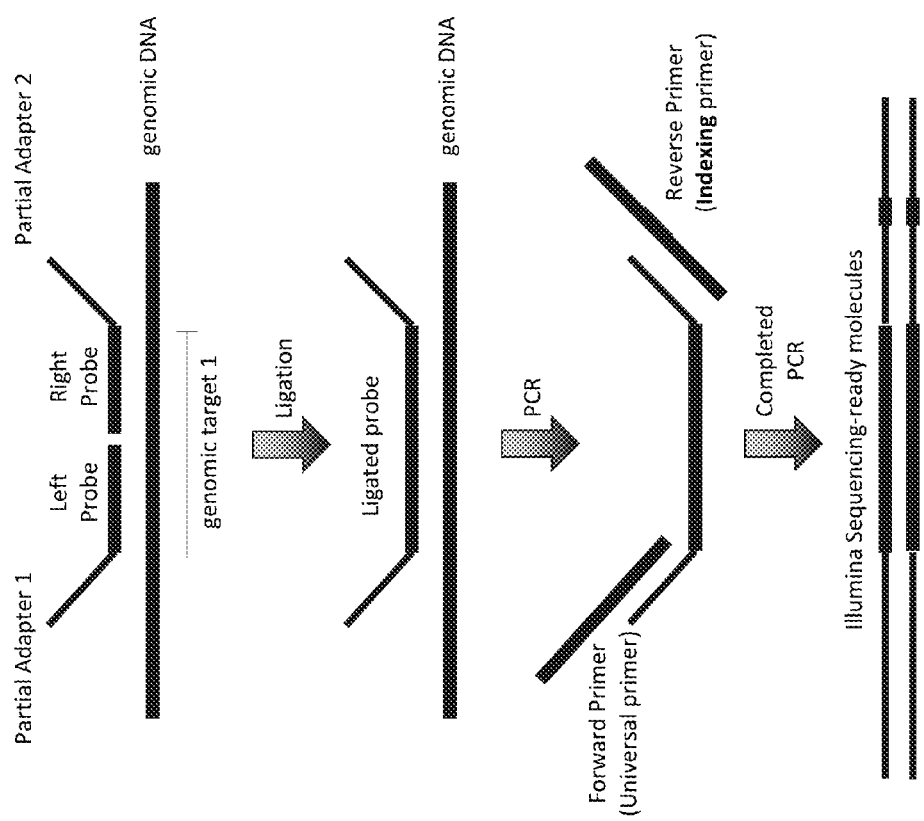
FIG. 3 shows a flow diagram for MLPA-SBS employing indexing, in accordance with embodiments disclosed herein.

Referring now to FIG. 2, there is shown a flow scheme summarizing an exemplary method for the MLPA-SBS assay, in accordance with embodiments disclosed herein. As indicated in FIG. 2, a query sample of DNA is hybridized with probe set comprising 5' and 3' half-probes (left probe and right probe) which hybridize across a genomic target. The half-probes are selected to be adjacent to each other on the genomic target, thus allowing for ligation of the probe set. The half-probes are also provided with adapter sequences which will be used in PCR amplification. After ligation, the ligated probe set is PCR amplified with the aid of modified forward and reverse primers. These are universal primers selected to be complementary to the adapter sequences flanking the target specific portion of the half-probes. The amplicons generated by PCR amplification can then be sequenced. In some embodiments, suitable sequencing methods can include the Next Generation Sequencing (NGS) system developed by utilizing the MISEQ® or HISEQ® System platforms available from Illumina, Inc. (San Diego, Calif.). In some embodiments, such detection systems may comprise a fluidics handling system configured to perform cycles of sequencing by synthesis on an array comprising the plurality of amplicons, the detection system configured to direct radiation from a source to the array and to direct fluorescence emission from the array to a camera, and a system control interface configured to automatically modify the detection system to increase the exposure level of the radiation directed to the array and detect fluorescence emission from the array to the camera at the increased exposure. FIG. 3 shows a flow scheme for a similar method as that shown in FIG. 2 in which an indexing sequence is provided in the modified reverse primer. The sequence of the flow scheme is the same, but the indexing sequences appear in the resultant amplicons facilitating identification of target nucleic acids from multiple sources.

In some embodiments, methods disclosed herein may be used to query a plurality of different target nucleic acids that is greater than about 100 in single run. In some embodiments, methods disclosed herein may be used to query a plurality of different target nucleic acids that is in a range from about 50 to about 100 target nucleic acids in a single run. In some embodiments, methods disclosed herein may be used to query a plurality of different target nucleic acids that is in a range from about 100 to about 500 target nucleic acids in a single run. In some embodiments, methods disclosed herein may be used to query a plurality of different target nucleic acids that is in a range from about 100 to about 1,000 target nucleic acids in a single run. In some embodiments, methods disclosed herein may be used to query a plurality of different target nucleic acids that is in a range from about 100 to about $10^8$ target nucleic acids in a single run. In principal, the number of target nucleic acids that may be queried may be limited only by the availability of an appropriate probe set.

In some embodiments, methods disclosed herein may comprise determining the copy number for each of the plurality of different target nucleic acids. In some such embodiments, the readout from sequencing-by-synthesis can directly provide copy number information. In some embodiments, determining the copy number may be performed in the presence of a control and each target nucleic acid queried for copy number may be normalized based on this control. In some embodiments, determining copy number may be used to assess the presence of genetic disease associated with aberrant copy number variation (CNV). Thus, in some embodiments, there is provided a method of detecting a disease or disorder associated with aberrant CNV comprising determining the copy number of one or more target nucleic acids. In some such embodiments, the disease or disorder may include, without limitation, Duchenne Muscular Dystrophy (DMD), Becker Muscular Dystrophy (BMD), Spinal Muscular Atrophy (SMA), Charcot Marie Tooth disease (CMT), Hereditary Neuropathy with liability to Pressure Palsies (HNNP), breast cancer, ovarian cancer, prostate cancer, Familial Adenomatous Polyposis (FAP), and Nonpolyposis Colorectal Cancer (HNPCC). One skilled in the art will appreciate that these are merely exemplary diseases/disorders and aberrant copy number variation can occur in any gene resulting in any number of other disease conditions.

In some embodiments, CNV determination may be used in methods to diagnose and/or monitor the progression of a cancer. The underlying progression of genetic events which transform a normal cell into a cancer cell may be characterized by a shift from the diploid to anueploid state (Albertson et al. (2003), Nat Genet, Vol. 34, pp. 369-76 and Lengauer et al. (1998), Nature, Vol. 396, pp. 643-9). As a result of genomic instability, cancer cells accumulate both random and causal alterations at multiple levels from point mutations to whole-chromosome aberrations. Copy number variation in the diagnosis and/or monitoring of the progression of cancer includes, but is not limited to, detecting loss of heterozygosity (LOH) and homozygous deletions, which can result in the loss of tumor suppressor genes, and gene amplification events, which can result in cellular proto-oncogene activation.

In some embodiments, methods disclosed herein may comprise detecting a single nucleotide polymorphism. Polymorphism refers to the occurrence of two or more genetically determined alternative sequences or loci in a population. A polymorphic marker or site is the locus at which divergence occurs. In some embodiments, markers have at least two loci, each occurring at frequency of greater than about 1%, and in other embodiments, greater than 10% or 20% of a selected population. A polymorphism may comprise one or more base changes, an insertion, a repeat, or a deletion. A polymorphic locus may be as small as one base pair. Polymorphic markers may include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form may be arbitrarily designated as the reference form and other allelic forms are designated as alternative or variant loci. The allelic form occurring most frequently in a selected population is sometimes referred to as the wildtype form. Diploid organisms may be homozygous or heterozygous for allelic forms. A diallelic polymorphism has two forms. A triallelic polymorphism has three forms, and so on. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. Single nucleotide polymorphisms (SNPs) are positions at which two alternative bases occur at appreciable frequency (greater than about 1%) in the human population, and are the most common type of human genetic variation.

The term genotyping refers to the determination of the genetic information an individual carries at one or more positions in the genome. For example, genotyping may comprise the determination of which locus or loci an individual carries for a single SNP or the determination of which locus or loci an individual carries for a plurality of SNPs. For example, a particular nucleotide in a genome may be an A in some individuals and a C in other individuals. Those individuals who have an A at the position have the A locus and those who have a C have the C locus. In a diploid organism the individual will have two copies of the sequence containing the polymorphic position so the individual may have an A locus and a C locus or alternatively two copies of the A locus or two copies of the C locus. Those individuals who have two copies of the C locus are homozygous for the C locus, those individuals who have two copies of the A locus are homozygous for the C locus, and those individuals who have one copy of each locus are heterozygous. An array may be designed to distinguish among each of these three possible outcomes. A polymorphic location may have two or more possible locus and an array may be designed to distinguish between all possible combinations.

In some embodiments, methods disclosed herein may comprise determining a degree of methylation of at least a portion of the plurality of different target nucleic acids. DNA methylation in CpG islands in promoter regionS is associated with transcriptional silencing and other cellular processes. However, aberrant DNA methylation is associated with several inherited human diseases and methylation of CpG islands in tumor suppressor genes, in particular, has been implicated in tumorigenesis. Methylation specific MLPA (MS-MLPA) has been developed to detect epigenetic alterations in genes involved in numerous disorders (see, for example, Nygren et al. Nucleic Acids Res. 33:e128 (2005), the entire contents of which are incorporated herein by reference in its entirety). In MS-MLPA, the target nucleic acids contain a restriction site for the endonuclease HhaI, which recognizes unmethylated GCGC sequences. After the hybridization step, the annealed probe sets may be treated with HhaI which digests probe sets hybridized to unmethylated DNA, leaving undigested probe sets hybridized to methylated DNA. Thus, only probe sets associated with methylated DNA are amplified. The level of methylation can be quantitated by comparison with a control. In some embodiments, methods disclosed herein to determine degree of methylation may be used to diagnose Prader Willi syndrome (PWS) or Angelman syndrome (AS). In some embodiments, methods disclosed herein for the detection of degree of methylation may be used to evaluate hypermethylation of genes in tumors, such genes including without limitation, MGMT, TIMP3, and CDKN2A.

As will be appreciated by those skilled in the art, the methods described herein with respect to DNA can apply equally to RNA-based detection. Thus, in some embodiments, methods disclosed herein may comprise quantifying a target mRNA. Reverse transcriptase MLPA (RT-MLPA) is a variation on MLPA developed especially for mRNA profiling. RT-MLPA for mRNA detection and quantitation may be used in querying of various apoptosis and inflammation genes.

The MLPA ligase enzyme typically employed in MLPA does not ligate DNA oligos which are annealed to an RNA target. To circumvent this, RT-MLPA starts with a reverse transcriptase reaction employing RT-primers, which anneal directly adjacent to or even overlap with the probe recognition site, thus reverse transcribing short mRNA fragments into cDNA. As short cDNA fragments are already sufficient for the probes to bind, the influence of RNA degradation on RT-MLPA results is small.

After the RT reaction, RT-MLPA continues as in standard MLPA, starting with hybridization of probes to their target cDNA. In some embodiments, RT-MLPA probes are designed to include an exon boundary in their target sequence: one part of a probe may hybridize to the last 25 nucleotides of exon 1, while the other binds to the first 35 nucleotides of exon 2. Such an "intron spanning" design prevents the probe from generating a signal on contaminating genomic DNA that is often present in RNA samples.

In some embodiments, methods disclosed herein may be used to determine at least one of a copy number, the presence of a single nucleotide polymorphism, a degree of methylation, and a quantity of mRNA, or any combination thereof.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example I

Copy Number Variation in Duchenne Muscular Dystrophy (DMD) gene

This Example shows the use of MLPA-SBS to screen the 79 exon DMD gene in a single MLPA-SBS assay.

DNA from two Duchenne muscular dystrophy patients with known copy number variants in the DMD gene, and a normal control were purchased from a biological repository (on the worldwide web at http://wwwn.cdc.gov/dls/genetics/rmmaterials/pdf/duchenne_becker.pdf). Traditional MLPA probes designed against all exons of the DMD gene were purchased and hybridized to these genomic DNAs, and subjected to thermostable ligase (per protocols described on the worldwide web at http://www.mlpa.com). Post-ligation, reactions were PCR amplified with primers described indicated below:

Primer 1.0 modified with constant region

SEQ ID NO: 1
CACCGAGATCTACACTCTTTCCCTACACGACGCTCTTCCGATCTGGGTTC

CCTAAGGGTTGGA-3'

SBS index #1, modified with complement to reverse constant region

ACGACCGTGTCTAGCCTTCTCGTGTGCAGACTTGAGGTCAGTGTAGTGCT

AGAGCATACGGCAGAAGACGAAC-5'
(Index #1 primer, SEQ ID NO: 2)

.ACGACCGTGTCTAGCCTTCTCGTGTGCAGACTTGAGGTCAGTGCGGTTA

TAGAGCATACGGCAGAAGACGAAC-5'
(Index #6 primer, SEQ ID NO: 3)

.ACGACCGTGTCTAGCCTTCTCGTGTGCAGACTTGAGGTCAGTGGAACAT

TAGAGCATACGGCAGAAGACGAAC-5'
(Index #12 primer, SEQ ID NO: 4)

Ed probe example. Two oligonucleotides are shown which represent MRC-holland DMD probe pair #01691-L00465. The underlined region ideize to the genome, while the highlighted regions are constant to all the MLPA probe oligonucleotides. The potential ligation is denoted by "-"

Sed for amplifying the ligated MLPA probes, and simultaneously preparing them for multiplexed SBS sequencing on the Illumina eq system.

Figure 4:
FIG. 4 shows a plot of read count versus exon number for the 79 exons associated with the Duchenne Muscular Dystrophy (DMD) gene demonstrating the use of a single-run MLPA-SBS system to detect copy number variation in male, female, and control samples, in accordance with embodiments disclosed herein.
Figure 5:
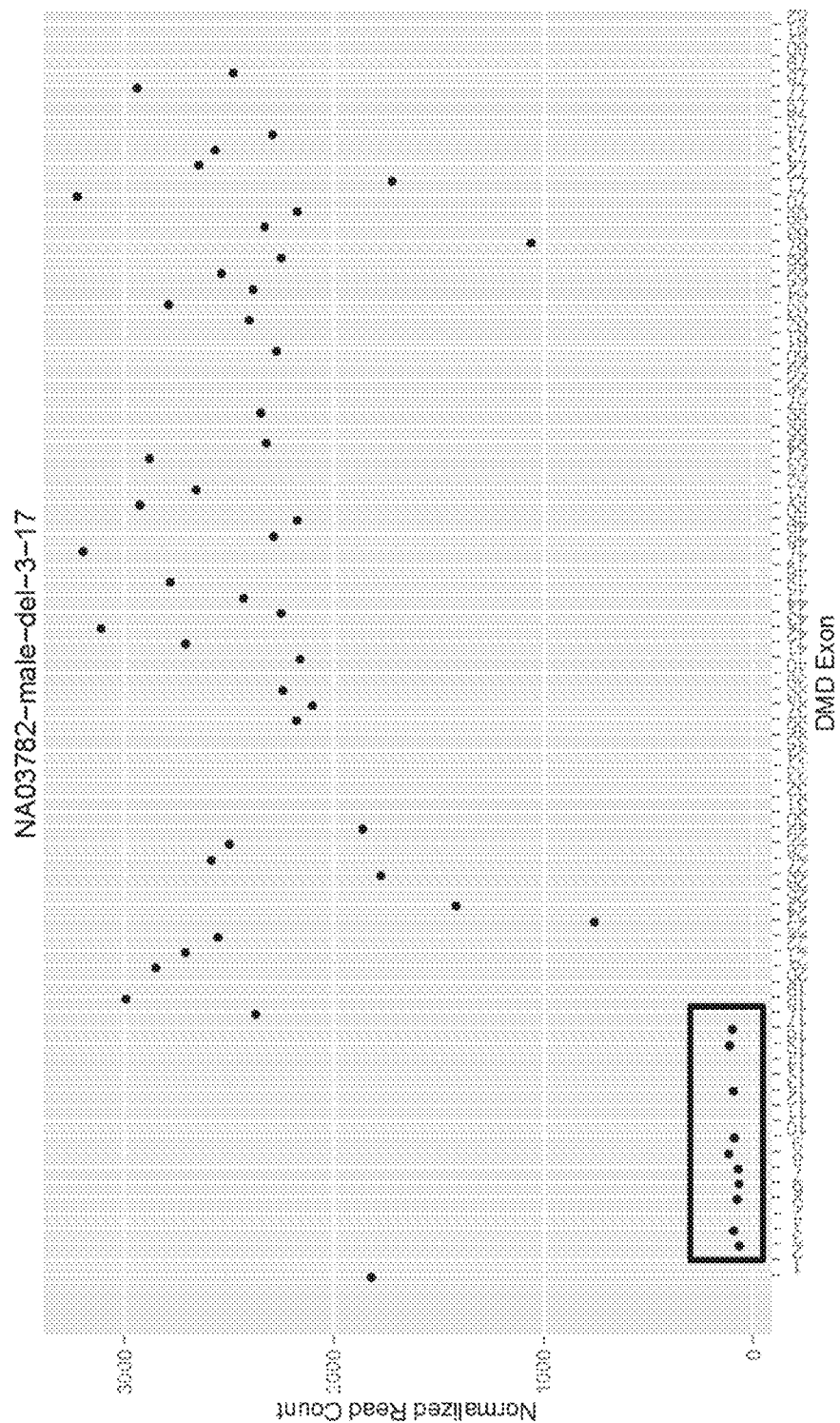
FIG. 5 shows another example as in FIG. 4 of normalized read counts versus exon numbers in the DMD gene. Female samples are in the upper facet and male samples are shown in the lower facet. Highlighted in the box are read counts from a male (Coriell DNA sample id NA03782) with a deletion in exons 3 through 17.
Figure 6:
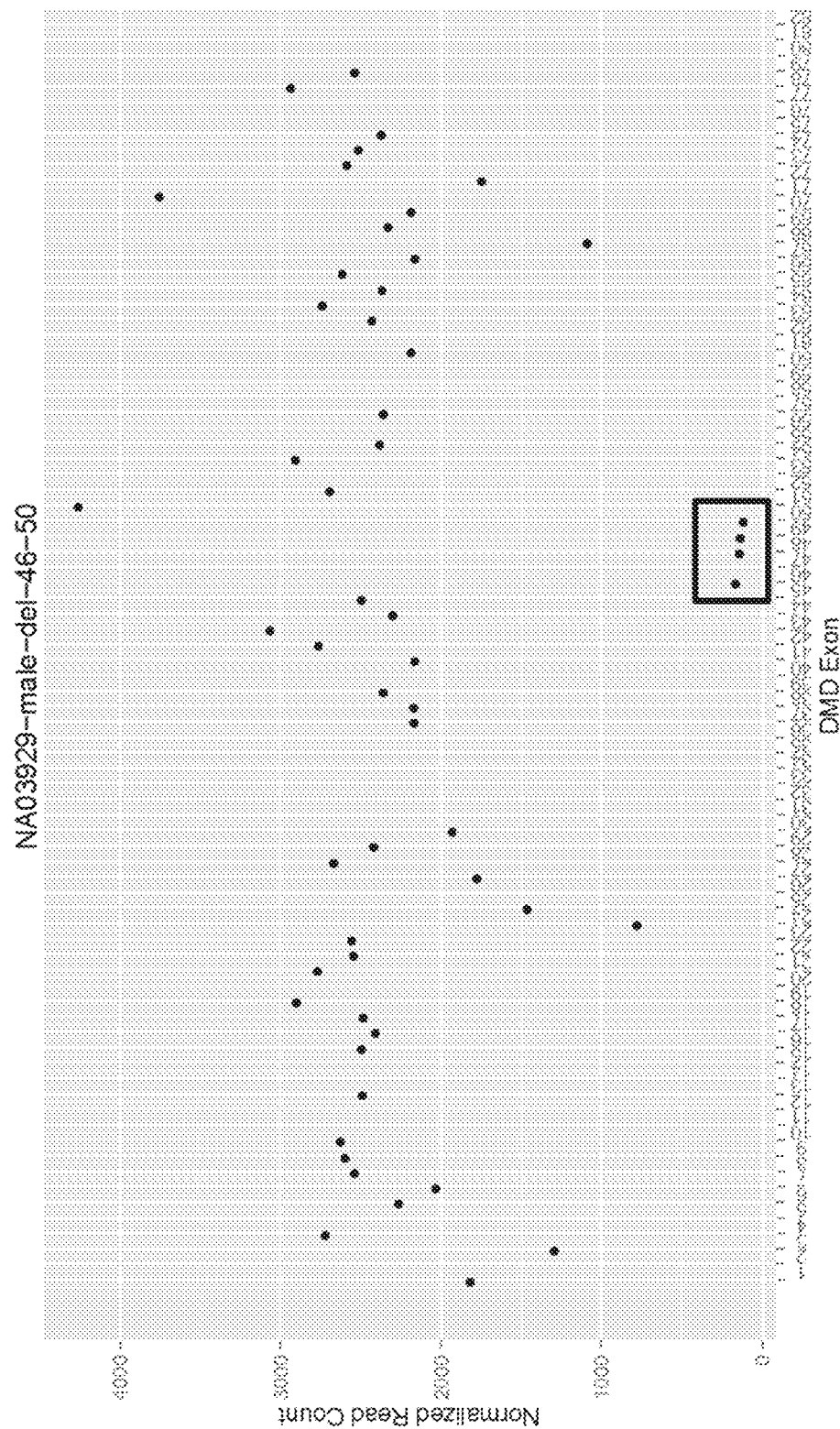
FIG. 6 shows another example as in FIG. 5 of normalized read counts versus exon numbers in the DMD gene. Highlighted in the box are read counts from a male (Coriell DNA sample id NA03929) with a deletion in exons 46 through 50.
Figure 7:
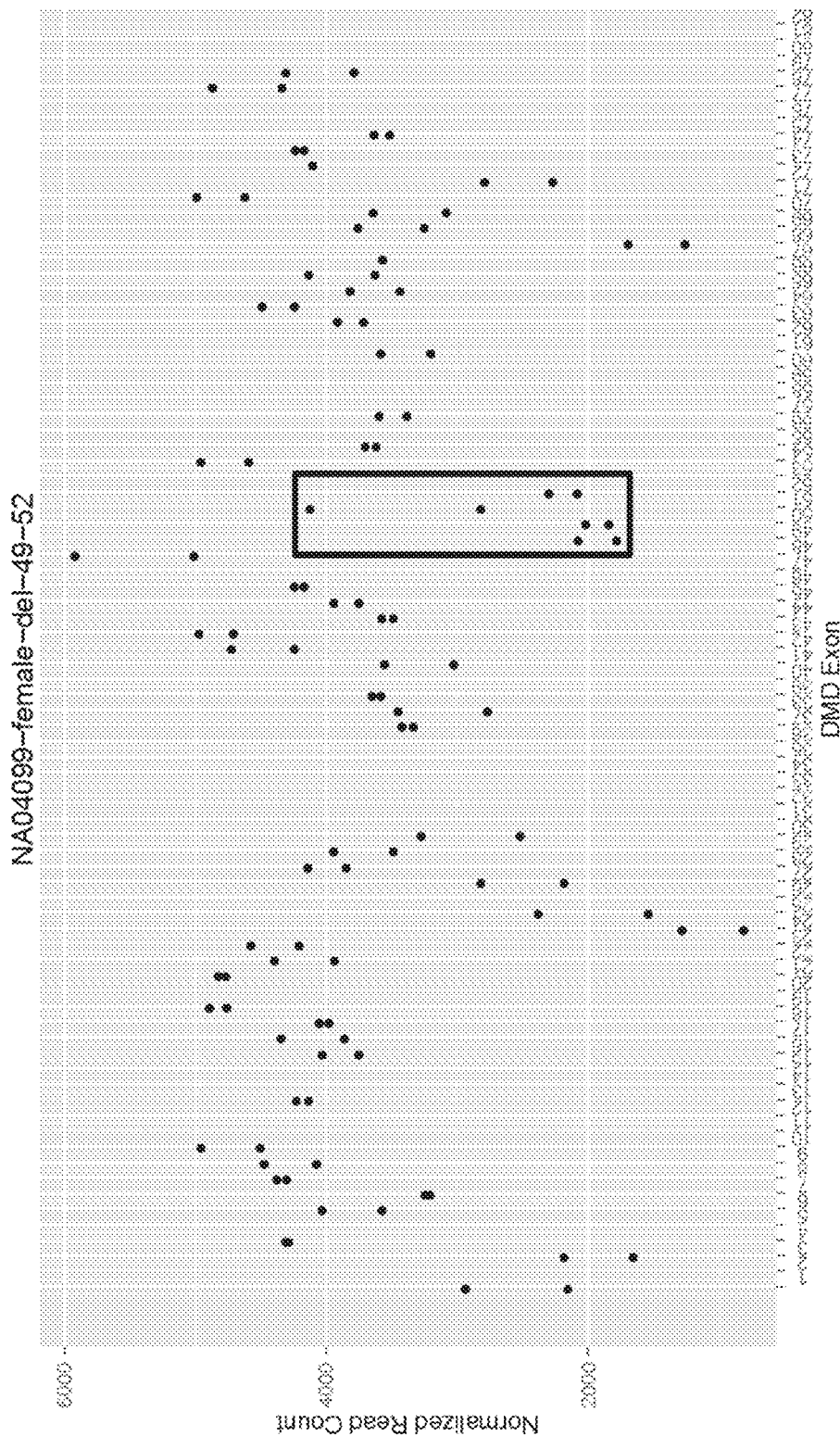
FIG. 7 shows another example as in FIG. 5 of normalized read counts versus exon numbers in the DMD gene. Highlighted in the box are read counts from a female (Coriell DNA sample id NA04099) with a deletion in exons 49 through 52.
Figure 8:
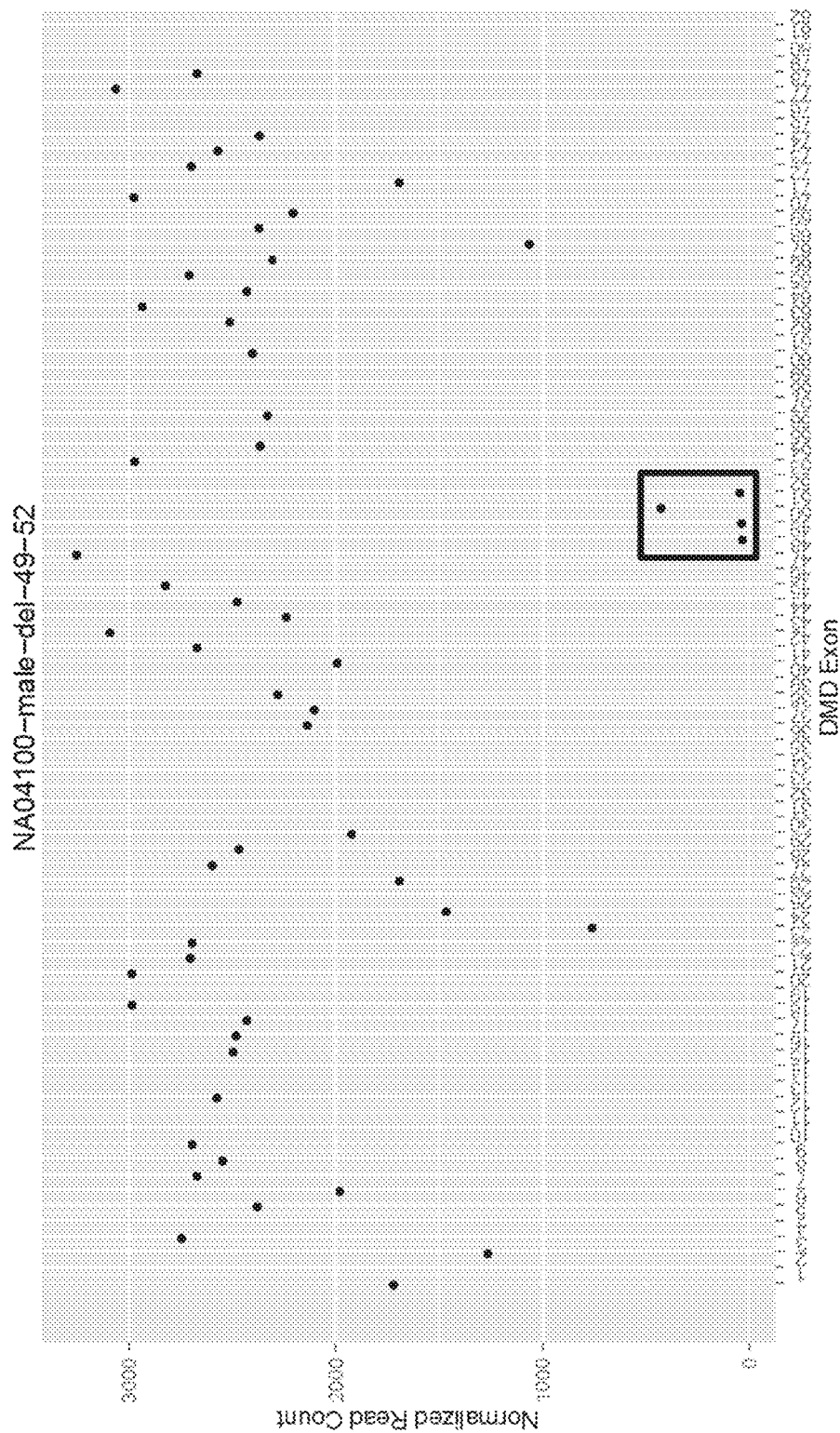
FIG. 8 shows another example as in FIG. 5 of normalized read counts versus exon numbers in the DMD gene. Highlighted in the box are read counts from a male (Coriell DNA sample id NA04100, son of NA04099) with a deletion in exons 49 through 52.
Figure 9:
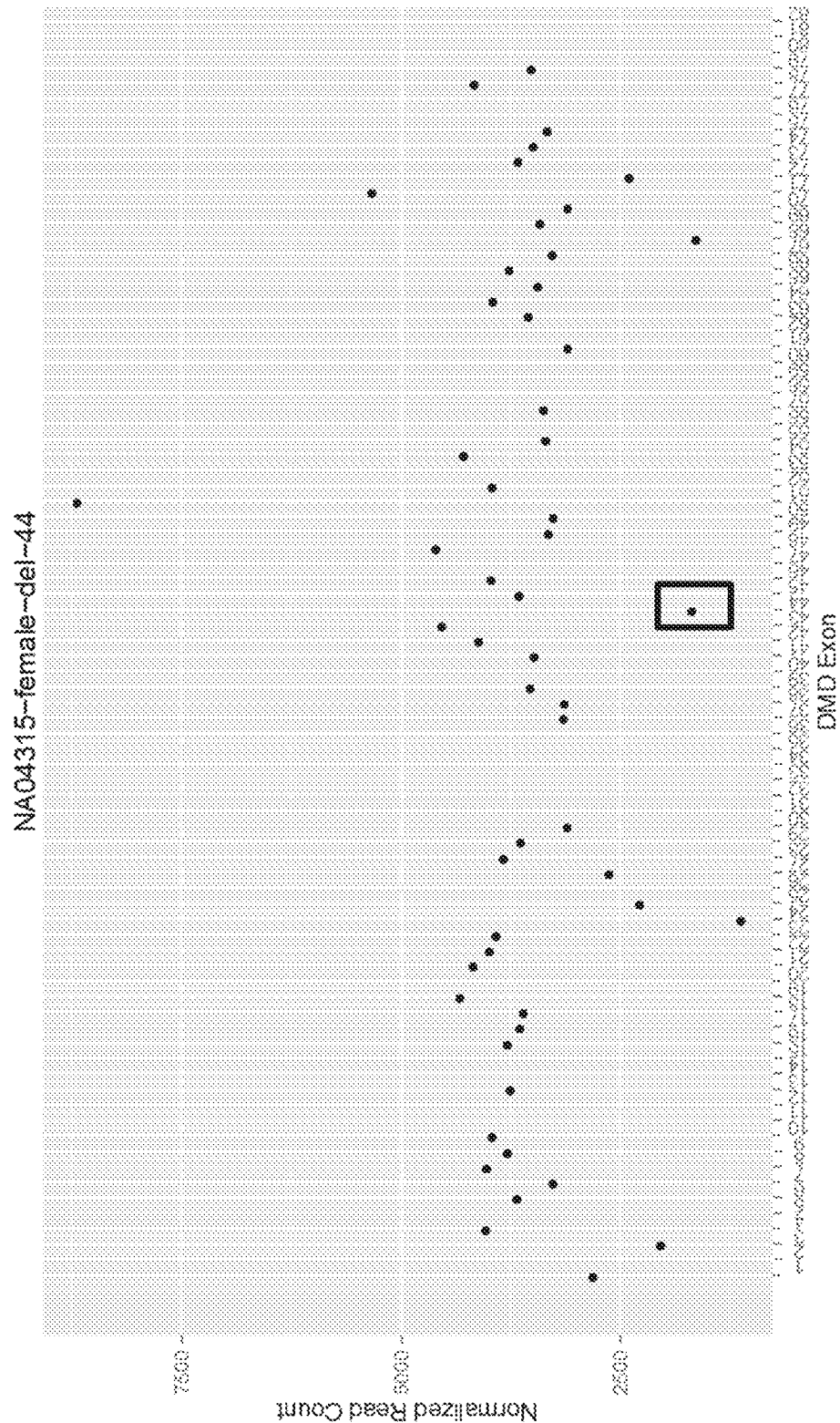
FIG. 9 shows another example as in FIG. 5 of normalized read counts versus exon numbers in the DMD gene. Highlighted in the box are read counts from a female (Coriell DNA sample id NA04315) with a deletion in exon 44.
Figure 10:
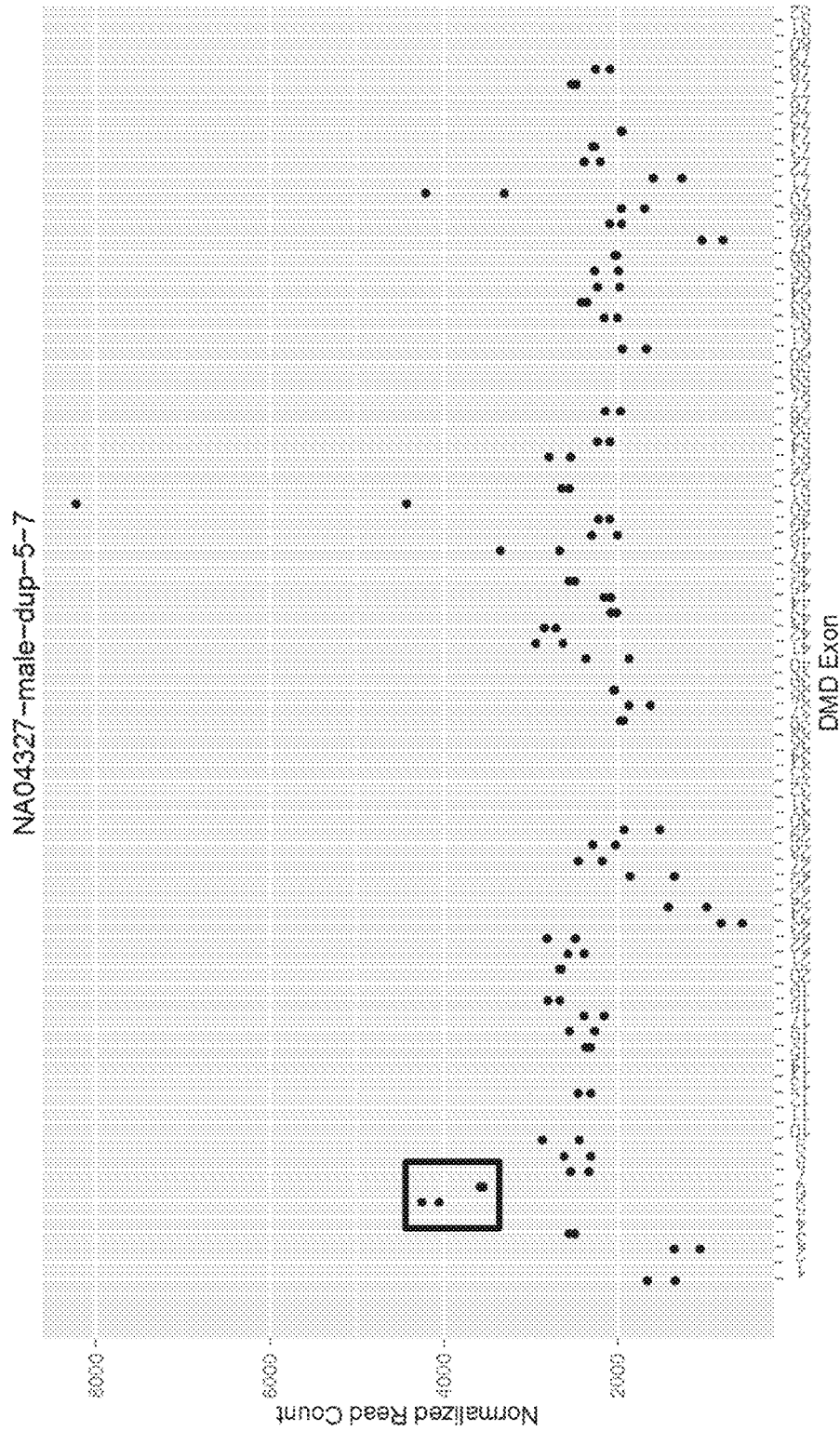
FIG. 10 shows another example as in FIG. 5 of normalized read counts versus exon numbers in the DMD gene. Highlighted in the box are read counts from a male (Coriell DNA sample id NA04327) with a duplication in exons 5 through 7.
Figure 11:
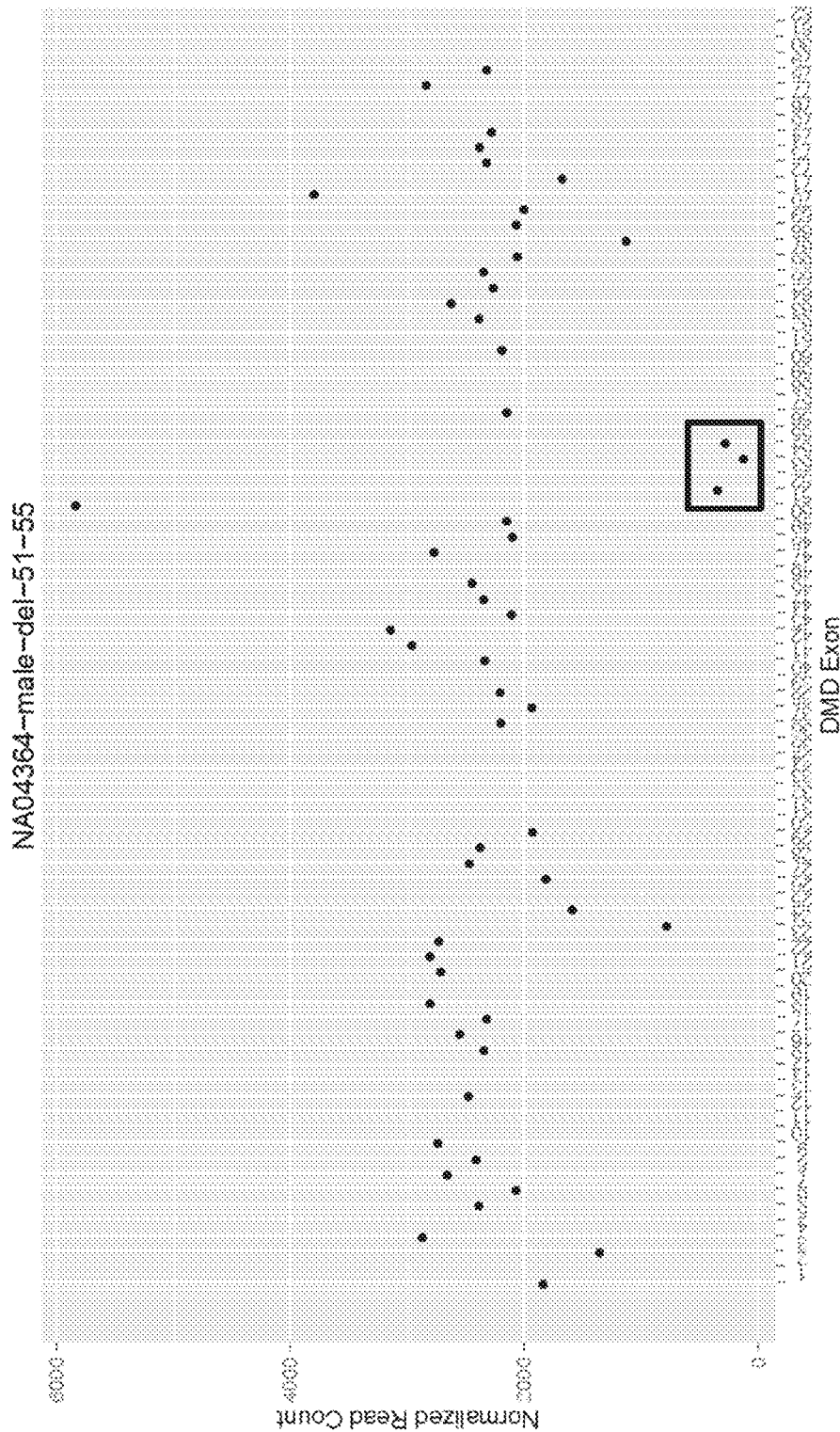
FIG. 11 shows another example as in FIG. 5 of normalized read counts versus exon numbers in the DMD gene. Highlighted in the box are read counts from a male (Coriell DNA sample id NA04364) with a deletion in exons 51 through 55.
Figure 12:
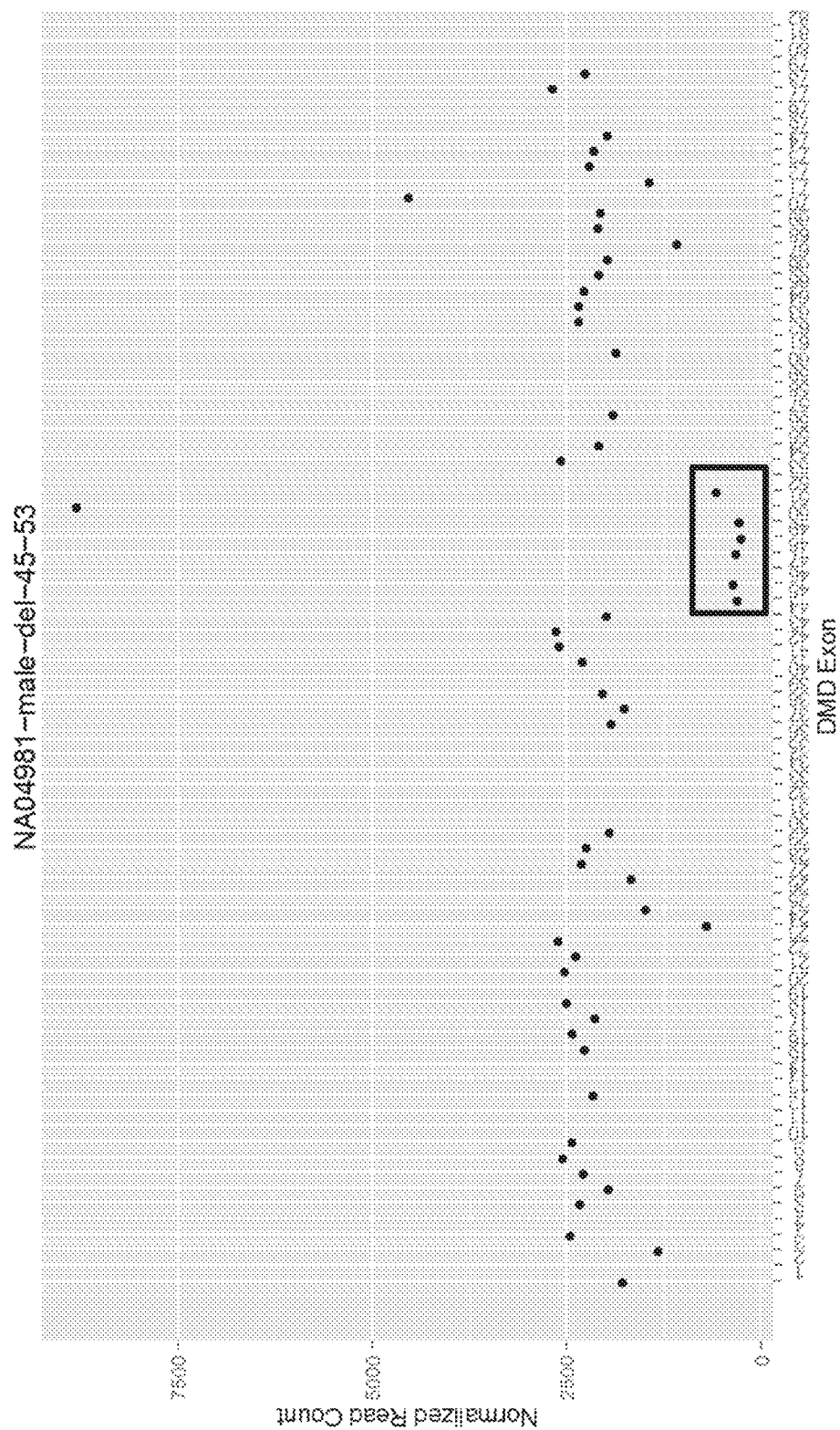
FIG. 12 shows another example as in FIG. 5 of normalized read counts versus exon numbers in the DMD gene. Highlighted in the box are read counts from a male (Coriell DNA sample id NA04981) with a deletion in exons 45 through 53.

These primers were designed to 1) batch amplify all successfully ligated MLPA probes (via the constant regions), 2) add Illumina-specific adapter sequences to enable SBS, and 3) apply sample specific barcodes for sample-sample identification on the pooled sequencing run. Post amplification products were purified, quantitated, and sequenced together on the Illumina MiSeq (San Diego, Calif.). Sequence reads were aligned to the human genome, and the numbers of reads mapping to each DMD probe were counted, normalized, and plotted as in FIG. 4. It is evident from the plot in FIG. 4 that the normalized read counts revealed a complete deletion in exons 49-52 for the male patient, and a heterozygous deletion in exons 49-52 for the female carrier patient (the mother of the male patient). DMD is an X-linked gene and thus a deletion will manifest in males as zero read count, while in a carrier female will manifest as a read count of roughly half of the control. These annotations match those of the original patient genotypes obtained from the genetic repository, and thus demonstrate the detection of copy number via MLPA-SBS.

Example II

MLPA Proof of Principle

This Example shows the use of highly multiplexed MLPA using a commercial system (Illumina, Inc., San Diego, Calif.) for the readout.

Stuffer-free probes for DMD, BRCA½, PMS2, SMN½, and control genes were designed as follows. Left and right probe sequences (LPO and RPO) were appended with sequences enabling amplification with Illumina indexing primers. For each probe pair, the LPO sequence (which anneals to the genome) was appended at its 5' end to create the following oligonucleotide: 5'-ACACTCTTTC-CCTACACGACGCTCTTCCGATCT-[LPO]-3', SEQ ID N0:5. Similarly, the RPO in each probe pair was appended at it's 3' end to create the following oligonucleotide 5'-P-[RPO]-AGATCGGAAGAGCACACGTCT-GAACTCCAGTCAC-3', SEQ ID N0:6. This RPO oligonucleotide is also modified with a 5' phosphate to facilitate ligation upon annealing adjacent to the LPO.

Partial left adapter:

SEQ ID NO: 7
5'-ACACTCTTTCCCTACACGACGCTCTTCCGATCT-LPO,

LPO is Left probe oligonucleotide that corresponds to complementary sequence that anneals to the genomic DNA target.

Partial Right adapter (with 5' phosphate indicated as "P"):

SEQ ID NO: 8
P-RPO-AGATCGGAAGAGCACACGTCTGAACTCCAGTCAC-3',

RPO=Right probe oligonucleotide that corresponds to complementary sequences that anneals to the genomic DNA target directly adjacent to the LPO.

Two hundred and fifty seven probe pairs were synthesized and pooled in equimolar quantities using standard oligonucleotide synthesis.

The above described pool of probe pairs was hybridized to denatured genomic DNA, annealed probe pairs were ligated and amplified using the primers described below.

Following successful hybridization and ligation, the probe pair has the following configuration:

SEQ ID NO: 9
5'-ACACTCTTTCCCTACACGACGCTCTTCCGATCT-LPO-RPO-

AGATCGGAAGAGCACACGTCTGAACTCCAGTCAC-'3,

Post ligation amplification with primers indicated adds additional sequences required for Illumina sequencing, specifically flow-cell amplification and multiplex identification of samples.

SEQ ID NO: 10
AATGATACGGCGACCACCGAGATCT
*ACACTCTTTCCCTACACGACGCTCTT*
***CCGATCT*,**

SEQ ID NO: 11
_ACACTCTTTCCCTACACGACGCTCTTCCGATCT_-LPO-RPO-
AGATCGGAAGAGCACACGTCT_GAACTCCAGTCAC_,

SEQ ID NO: 12
_CTTGAGGTCAGTG_(TAGTGC)TAGAGCATACGGCAGAA
GACGAAC,

SEQ ID NO: 13
PCR Primer, Index 1 (ATCACG)

This assay was performed on eight samples containing previously characterized copy number changes in the DMD gene. The products were sequenced on an Illumina MiSeq using a 50 bp single end run. Reads were mapped to a tag-based reference, hits to each tag were normalized to total yield for each sample. Normalized tag counts are shown in FIGS. 5 through 12. All eight events were easily detectable without sophisticated analysis of normalized read counts.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

All the patents and applications referred to herein are hereby specifically, and incorporated herein by reference in their entirety in the instant specification.

What is claimed is:

1. A method for multiplex ligation-dependent probe amplification comprising:
   (a) providing a sample tissue to query at least 100 different target nucleic acids;
   (b) providing a plurality of different probe sets for each of the at least 100 different target nucleic acids, wherein each probe set comprises:
      a first locus specific probe comprising a first adapter sequence and a first target specific portion; and
      a second locus specific probe comprising a second adapter sequence, and a second target specific portion adjacent to the first target specific portion;
   (c) hybridizing the plurality of different probe sets to the at least 100 different target sequences to form at least 100 different hybridization complexes;
   (d) ligating, in a single vessel or tube, the at least 100 different hybridization complexes to form at least 100 different ligated probes;
   (e) amplifying the at least 100 different ligated probes to form at least 100 different amplicons, wherein (i) the amplifying step is carried out with a first universal primer comprising a region complementary to the first adapter sequence and a second universal primer comprising a region complementary to the second adapter sequence, and (ii) the amplifying of the at least 100 different ligated probes is carried out in the single vessel or tube; and
   (f) detecting the at least 100 different amplicons in a detection system, independently of the length, by sequencing each of the at least 100 different amplicons wherein said at least 100 different ligated probes of step (d) are directly amplified in step (e) without purification.

2. The method of claim 1, further comprising determining the copy number for each of the at least 100 different target nucleic acids.

3. The method of claim 1, wherein the at least 100 different target nucleic acids is at least 1000 different target nucleic acids, the at least 100 different hybridization complexes is at least 1000 different hybridization complexes, the at least 100 different ligated probes is at least 1000different ligated probes, and the at least 100 different amplicons is at least 1000 different amplicons.

4. The method of claim 1, wherein the at least 100 different target nucleic acids is in a range from about 100 to about 500 target nucleic acids, the at least 100 different hybridization complexes is in a range from about 100 to about 500 different hybridization complexes, the at least 100 different ligated probes is in a range from about 100 to about 500 different ligated probes, and the at least 100 different amplicons is in a range from about 100 to about 500 different amplicons.

5. The method of claim 1, wherein the at least 100 different target nucleic acids is in a range from about 100 to about 1,000 target nucleic acids, the at least 100 different hybridization complexes is in a range from about 100 to about 1,000 different hybridization complexes, the at least 100 different ligated probes is in a range from about 100 to about 1,000 different ligated probes, and the at least 100 different amplicons is in a range from about 100 to about 1,000 different amplicons.

6. The method of claim 1, wherein the at least 100 different target nucleic acids is in a range from about 100 to about $10^8$ target nucleic acids, the at least 100 different hybridization complexes is in a range from about 100 to about $10^8$ different hybridization complexes, the at least 100 different ligated probes is in a range from about 100 to about $10^8$ different ligated probes, and the at least 100 different amplicons is in a range from about 100 to about $10^8$ different amplicons.

7. The method of claim 1, wherein at least one of the first universal primer and the second universal primer further comprises an indexing sequence.

8. The method of claim 1, wherein the detection system comprises sequencing by synthesis.

9. The method of claim 8, wherein the detection system comprises a fluidics handling system configured to perform cycles of sequencing by synthesis on an array comprising the at least 100 different amplicons, the detection system configured to direct radiation from a source to the array and to direct fluorescence emission from the array to a camera, and a system control interface configured to automatically modify the detection system to increase the exposure level of the radiation directed to the array and detect fluorescence emission from the array to the camera at the increased exposure.

10. The method of claim 1, wherein the method comprises detecting a single nucleotide polymorphism.

11. The method of claim 1, wherein the method comprises determining a degree of methylation of at least a portion of the at least 100 different target nucleic acids.

12. The method of claim 1, wherein the method comprises quantifying a target mRNA.

13. The method of claim 1, wherein the hybridizing of (c), the ligating of (d) and the amplifying of (e) are carried out in the single vessel or tube.

14. A method for multiplex ligation-dependent probe amplification comprising:
(a) contacting at least 100 different target nucleic acids with at least 100 different probe sets for each of the different target nucleic acids, wherein each probe set comprises,
(i) a first locus specific probe comprising a first adapter sequence and a first target specific portion, and
(ii) a second locus specific probe comprising a second adapter sequence, and a second target specific portion adjacent to the first target specific portion,
wherein the probe sets hybridize to the target sequences thereby forming at least 100 different hybridization complexes in a single mixture, wherein the at least 100 different hybridization complexes comprise the at least 100 different target nucleic acids and the at least 100 different probe sets;
(b) ligating the at least 100 different hybridization complexes in the mixture, thereby providing at least 100 different ligated probes comprised in the mixture;
(c) amplifying the at least 100 different ligated probes in the mixture to form at least 100 different amplicons, wherein the amplifying is carried out with a first universal primer comprising a region complementary to the first adapter sequence and a second universal primer comprising a region complementary to the second adapter sequence; and
(d) detecting the at least 100 different amplicons in the mixture in a detection system by sequencing each of the at least 100 different amplicons wherein said at least 100 different ligated probes of step (b) are directly amplified in step (c) without purification.

15. The method of claim 14, wherein the detection system comprises sequencing by synthesis.

* * * * *

SEQUENCE LISTING

```
<160> NUMBER OF SEQ ID NOS: 12

<210> SEQ ID NO 1
<211> LENGTH: 63
<212> TYPE: DNA
<213> ORGANISM: Artificial Sequence
<220> FEATURE:
<223> OTHER INFORMATION: Description of Sequence: Primer sequence

<400> SEQUENCE: 1
caccgagatc tacactcttt ccctacacga cgctcttccg atctgggttc cctaagggtt      60
gga                                                                    63

<210> SEQ ID NO 2
<211> LENGTH: 73
<212> TYPE: DNA
<213> ORGANISM: Artificial Sequence
<220> FEATURE:
<223> OTHER INFORMATION: Description of Sequence: Primer sequence

<400> SEQUENCE: 2
acgaccgtgt ctagccttct cgtgtgcaga cttgaggtca gtgtagtgct agagcatacg      60
gcagaagacg aac                                                         73

<210> SEQ ID NO 3
<211> LENGTH: 73
<212> TYPE: DNA
<213> ORGANISM: Artificial Sequence
<220> FEATURE:
<223> OTHER INFORMATION: Description of Sequence: Primer sequence

<400> SEQUENCE: 3
acgaccgtgt ctagccttct cgtgtgcaga cttgaggtca gtgcggttat agagcatacg      60
gcagaagacg aac                                                         73

<210> SEQ ID NO 4
<211> LENGTH: 73
<212> TYPE: DNA
<213> ORGANISM: Artificial Sequence
<220> FEATURE:
<223> OTHER INFORMATION: Description of Sequence: Primer sequence
```

-continued

```
<400> SEQUENCE: 4
acgaccgtgt ctagccttct cgtgtgcaga cttgaggtca gtggaacatt agagcatacg      60
gcagaagacg aac                                                        73

<210> SEQ ID NO 5
<211> LENGTH: 33
<212> TYPE: DNA
<213> ORGANISM: Artificial Sequence
<220> FEATURE:
<223> OTHER INFORMATION: Description of Sequence: Left probe
      oligonucleotide

<400> SEQUENCE: 5
acactctttc cctacacgac gctcttccga tct                                  33

<210> SEQ ID NO 6
<211> LENGTH: 34
<212> TYPE: DNA
<213> ORGANISM: Artificial Sequence
<220> FEATURE:
<223> OTHER INFORMATION: Description of Sequence: Right probe
      oligonucleotide

<400> SEQUENCE: 6
agatcggaag agcacacgtc tgaactccag tcac                                 34

<210> SEQ ID NO 7
<211> LENGTH: 33
<212> TYPE: DNA
<213> ORGANISM: Artificial Sequence
<220> FEATURE:
<223> OTHER INFORMATION: Description of Sequence: Left probe
      oligonucleotide

<400> SEQUENCE: 7
acactctttc cctacacgac gctcttccga tct                                  33

<210> SEQ ID NO 8
<211> LENGTH: 34
<212> TYPE: DNA
<213> ORGANISM: Artificial Sequence
<220> FEATURE:
<223> OTHER INFORMATION: Description of Sequence: Right probe
      oligonucleotide

<400> SEQUENCE: 8
agatcggaag agcacacgtc tgaactccag tcac                                 34

<210> SEQ ID NO 9
<211> LENGTH: 67
<212> TYPE: DNA
<213> ORGANISM: Artificial Sequence
<220> FEATURE:
<223> OTHER INFORMATION: Description of Sequence: Oligonucleotide probe
      pair

<400> SEQUENCE: 9
acactctttc cctacacgac gctcttccga tctagatcgg aagagcacac gtctgaactc      60
cagtcac                                                               67

<210> SEQ ID NO 10
<211> LENGTH: 58
<212> TYPE: DNA
<213> ORGANISM: Artificial Sequence
```

-continued

```
<220> FEATURE:
<223> OTHER INFORMATION: Description of Sequence: Oligonucleotide primer

<400> SEQUENCE: 10
aatgatacgg cgaccaccga gatctacact ctttccctac acgacgctct tccgatct        58

<210> SEQ ID NO 11
<211> LENGTH: 67
<212> TYPE: DNA
<213> ORGANISM: Artificial Sequence
<220> FEATURE:
<223> OTHER INFORMATION: Description of Sequence: Oligonucleotide probe
      pair

<400> SEQUENCE: 11
acactctttc cctacacgac gctcttccga tctagatcgg aagagcacac gtctgaactc      60
cagtcac                                                               67

<210> SEQ ID NO 12
<211> LENGTH: 43
<212> TYPE: DNA
<213> ORGANISM: Artificial Sequence
<220> FEATURE:
<223> OTHER INFORMATION: Description of Sequence: Oligonucleotide primer

<400> SEQUENCE: 12
cttgaggtca gtgtagtgct agagcatacg gcagaagacg aac                       43
```